(12) United States Patent
Kamalova

(10) Patent No.: US 12,023,054 B2
(45) Date of Patent: Jul. 2, 2024

(54) CATHETER APPARATUS

(71) Applicant: Flow Medical Corporation, Wilmington, DE (US)

(72) Inventor: Marina Kamalova, Tbilisi (GE)

(73) Assignee: SCP Altis, Monaco (MC)

( * ) Notice: Subject to any disclaimer, the term of this patent is extended or adjusted under 35 U.S.C. 154(b) by 493 days.

(21) Appl. No.: 17/278,873

(22) PCT Filed: Sep. 30, 2019

(86) PCT No.: PCT/US2019/053871
§ 371 (c)(1),
(2) Date: Mar. 23, 2021

(87) PCT Pub. No.: WO2020/069521
PCT Pub. Date: Apr. 2, 2020

(65) Prior Publication Data
US 2022/0047281 A1     Feb. 17, 2022

Related U.S. Application Data

(60) Provisional application No. 62/738,137, filed on Sep. 28, 2018.

(51) Int. Cl.
*A61B 17/22* (2006.01)
*A61M 25/00* (2006.01)
*A61M 25/09* (2006.01)

(52) U.S. Cl.
CPC ......... *A61B 17/22* (2013.01); *A61M 25/0026* (2013.01); *A61M 25/09* (2013.01);
(Continued)

(58) Field of Classification Search
CPC .......... A61B 17/22; A61B 2017/22079; A61B 2017/32032; A61B 2017/320084;
(Continued)

(56) References Cited

U.S. PATENT DOCUMENTS

| 5,318,518 A |   | 6/1994 | Plechinger |
| 5,441,482 A | * | 8/1995 | Clague .................... A61M 1/85 604/35 |

(Continued)

FOREIGN PATENT DOCUMENTS

| CA | 2552859 | 8/2005 |
| CN | 210228259 | 4/2020 |

(Continued)

OTHER PUBLICATIONS

Official Action dated May 10, 2022 issued by the Japanese Patent Office in Japanese Patent Application No. 2021-542075.
(Continued)

*Primary Examiner* — Shaun L David
*Assistant Examiner* — Rachael L Geiger
(74) *Attorney, Agent, or Firm* — Billion & Armitage

(57) ABSTRACT

A suction catheter for fragmenting and removing obstructive material and thrombus from the body or other body cavities that comprises a tube-like body with a proximal and distal end and a pressure lumen and discharge lumen formed in the catheter body. At the distal end of the catheter is a suction opening adjacent to the opening of the nozzle injector formation. At the proximal end of the catheter the lumens are connected to an inlet port and a discharge outlet. A hub structure is coupled to the proximal end of the catheter tubular body and includes a pressure lumen for connecting a fluid source to the pressure inlet. At the proximal end of the tubular catheter a discharge lumen is connected at the proximal hub to a discharge reservoir. The suction port at the distal end of the catheter may be formed into a separate lumen within the catheter body and may include a guidewire lumen.

7 Claims, 7 Drawing Sheets

(52) U.S. Cl.
CPC .............. *A61B 2017/22079* (2013.01); *A61M 2025/091* (2013.01); *A61M 2205/02* (2013.01)

(58) Field of Classification Search
CPC  A61B 2017/32035; A61B 2017/32007; A61B 17/3203; A61B 17/32037; A61M 25/0026; A61M 25/09; A61M 2025/091; A61M 2205/02; A61M 1/85; A61M 1/87; A61M 2025/0031; A61M 25/003; A61M 1/777; A61M 1/774; A61M 1/77
See application file for complete search history.

(56) References Cited

U.S. PATENT DOCUMENTS

| | | | |
|---|---|---|---|
| 5,713,849 A * | 2/1998 | Bosma | A61M 1/85 604/35 |
| 5,931,831 A | 8/1999 | Linder | |
| 6,729,334 B1 | 5/2004 | Baran | |
| 9,737,328 B2 | 8/2017 | Bonnette et al. | |
| 9,789,029 B2 | 10/2017 | Besser et al. | |
| 9,895,483 B2 | 2/2018 | Shtul et al. | |
| 10,500,360 B1 | 12/2019 | Zchar | |
| 10,702,638 B2 | 7/2020 | Pastron | |
| 10,835,269 B1 | 11/2020 | Wallace et al. | |
| 2001/0051811 A1* | 12/2001 | Bonnette | A61M 1/85 604/35 |
| 2006/0229550 A1* | 10/2006 | Staid | A61B 17/3203 604/27 |
| 2007/0227543 A1 | 10/2007 | Peichel | |
| 2008/0025596 A1 | 10/2008 | Jenson et al. | |
| 2009/0107503 A1 | 4/2009 | Baran | |
| 2013/0267891 A1* | 10/2013 | Malhi | A61B 17/32037 604/30 |
| 2014/0012882 A1 | 5/2014 | Odland et al. | |
| 2014/0194916 A1* | 7/2014 | Ichikawa | A61B 17/3203 606/180 |
| 2017/0258484 A1* | 9/2017 | Staid | A61B 17/3203 |
| 2018/0015255 A1 | 1/2018 | Bonnette et al. | |
| 2018/0235648 A1 | 8/2018 | Wilke et al. | |
| 2019/0038300 A1 | 2/2019 | Savastano et al. | |
| 2019/0274704 A1 | 9/2019 | Jenson et al. | |
| 2019/0290315 A1 | 9/2019 | Bonnette et al. | |
| 2019/0298435 A1 | 10/2019 | Estevez et al. | |
| 2019/0307943 A1 | 10/2019 | Franano et al. | |
| 2019/0314077 A1 | 10/2019 | Razavi et al. | |
| 2019/0314561 A1 | 10/2019 | Pacey | |
| 2019/0321575 A1 | 10/2019 | White et al. | |
| 2019/0321588 A1 | 10/2019 | Burnett et al. | |
| 2019/0321589 A1 | 10/2019 | Bonneau | |
| 2019/0351181 A1 | 11/2019 | Dubielzig et al. | |
| 2019/0365404 A1 | 12/2019 | Ryan, Jr. | |
| 2019/0381223 A1 | 12/2019 | Culbert et al. | |
| 2019/0381287 A1 | 12/2019 | Mock et al. | |
| 2019/0388604 A1 | 12/2019 | Kelly et al. | |
| 2020/0000059 A1 | 1/2020 | Salahieh et al. | |
| 2020/0002317 A1 | 1/2020 | Blanchard et al. | |
| 2020/0015889 A1 | 1/2020 | Smith et al. | |
| 2020/0022711 A1 | 1/2020 | Look et al. | |
| 2020/0023110 A1 | 1/2020 | Jahangir | |
| 2020/0046368 A1 | 2/2020 | Merritt et al. | |
| 2020/0050222 A1 | 2/2020 | Lane et al. | |
| 2020/0060746 A1 | 2/2020 | Harmouche | |
| 2020/0069312 A1 | 3/2020 | Lenneman et al. | |
| 2020/0100716 A1 | 4/2020 | Devgon et al. | |
| 2020/0101272 A1 | 4/2020 | Kuperberg | |
| 2020/0129194 A1 | 4/2020 | Wallace et al. | |
| 2020/0206457 A1 | 7/2020 | Boling | |
| 2020/0230371 A1 | 7/2020 | Klausen et al. | |

FOREIGN PATENT DOCUMENTS

| | | |
|---|---|---|
| CN | 210228842 | 4/2020 |
| CN | 210277287 | 4/2020 |
| CN | 111096901 | 5/2020 |
| CN | 210433777 | 5/2020 |
| CN | 210447130 | 5/2020 |
| CN | 111419338 | 7/2020 |
| CN | 210963234 | 7/2020 |
| EP | 2620110 | 7/2013 |
| EP | 3656414 | 5/2020 |
| JP | 2003260127 | 9/2003 |
| JP | 2003290236 A | 10/2003 |
| JP | 2006314854 | 11/2006 |
| JP | 2007517611 A | 7/2007 |
| JP | 2010517642 A | 5/2010 |
| JP | 2013154171 | 8/2013 |
| WO | 2019195028 | 10/2019 |
| WO | 2019199931 | 10/2019 |
| WO | 2019222335 | 11/2019 |
| WO | 2019236735 | 12/2019 |
| WO | 2019236737 | 12/2019 |
| WO | 2020008488 | 1/2020 |
| WO | 2020012321 | 1/2020 |
| WO | 2020014764 | 1/2020 |
| WO | 2020046023 | 3/2020 |
| WO | 2020046265 | 3/2020 |
| WO | 2020049000 | 3/2020 |
| WO | 2020064660 | 4/2020 |
| WO | 2020069216 | 4/2020 |
| WO | 2020076990 | 4/2020 |
| WO | 2020092959 | 5/2020 |
| WO | 2020099386 | 5/2020 |
| WO | 2020112622 | 6/2020 |
| WO | 2020113957 | 6/2020 |
| WO | 2020117844 | 6/2020 |
| WO | 2020123589 | 6/2020 |
| WO | 2020123791 | 6/2020 |
| WO | 2020132003 | 6/2020 |
| WO | 2020142846 | 7/2020 |
| WO | 2020146454 | 7/2020 |
| WO | 2020149873 | 7/2020 |
| WO | 2020149416 | 11/2021 |

OTHER PUBLICATIONS

Official Action dated Apr. 26, 2022 issued by the Chinese Patent Office in Chinese Patent Application No. 201980064015.5.
Supplementary Search Report and Preliminary Opinion dated Jun. 3, 2022 issued by the European Patent Office in European Patent Application No. 19867438.4.
International Search Report and Written Opinion dated Nov. 4, 2019 in International Patent Application No. PCT/US2019/053871.
Translation of JP Office Action for Application No. 2021-542075; dated Nov. 9, 2022; 3 pages.
Hearing Notice dated Mar. 11, 2024 issued in Indian Patent Application No. 202127011582.

* cited by examiner

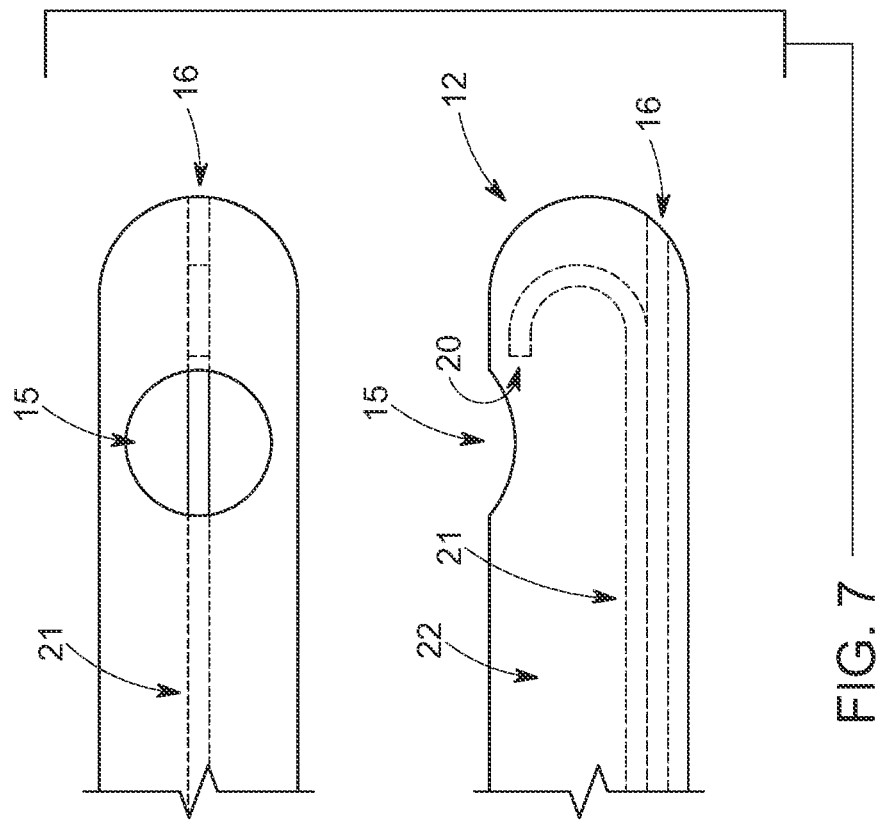
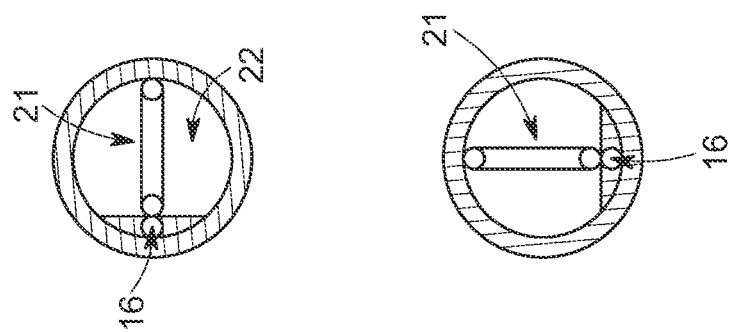
FIG. 7

CATHETER APPARATUS

FIELD OF THE INVENTION

The present invention relates to catheter systems generally, and more particularly to suction catheters useful in retrieving tissue from a treatment location in vivo.

BACKGROUND OF THE INVENTION

Hydrodynamic suction catheters, also known simply as suction catheters, are configured to enable the removal of material from a treatment site, and particularly from within body vessels. Such catheters typically include a suction opening adjacent to a jet nozzle for generating an environment external to the distal end of the catheter that induces fluid flow into the suction opening. Collected material and the pressurized fluid are returned in a proximal direction through the catheter to remove the collected material from the vessel.

Conventional suction catheters induce certain fluid dynamics surrounding the distal catheter tip which, while useful in collecting target material from the surrounding region, can disrupt and damage tissue cells as a result of the elevated shear stresses applied to such tissue. It is therefore an object of the invention to retain the functionality of removing substances from a body vessel with a catheter apparatus while avoiding unnecessary tissue damage in the process.

SUMMARY OF THE INVENTION

By means of the present invention, material at a treatment location in vivo may be collected and withdrawn from the body. A suction catheter apparatus of the present invention induces a low-shear stress fluidic environment surrounding a distal end of the apparatus that is nevertheless adequate to support collection of target tissue through a suction opening.

BRIEF DESCRIPTION OF THE DRAWINGS

FIG. 7 illustrates a top plan view and side elevational view of a distal end portion of a suction catheter apparatus of the present invention, along with rear cross-sectional views with respect to such orientations.

DETAILED DESCRIPTION OF THE PREFERRED EMBODIMENTS

The objects and advantages enumerated above together with other objects, features, and advances represented by the present invention will now be presented in terms of detailed embodiments described with reference to the attached drawing figures which are intended to be representative of various possible configurations of the invention. Other embodiments and aspects of the invention are recognized as being within the grasp of those having ordinary skill in the art.

Figure 1:
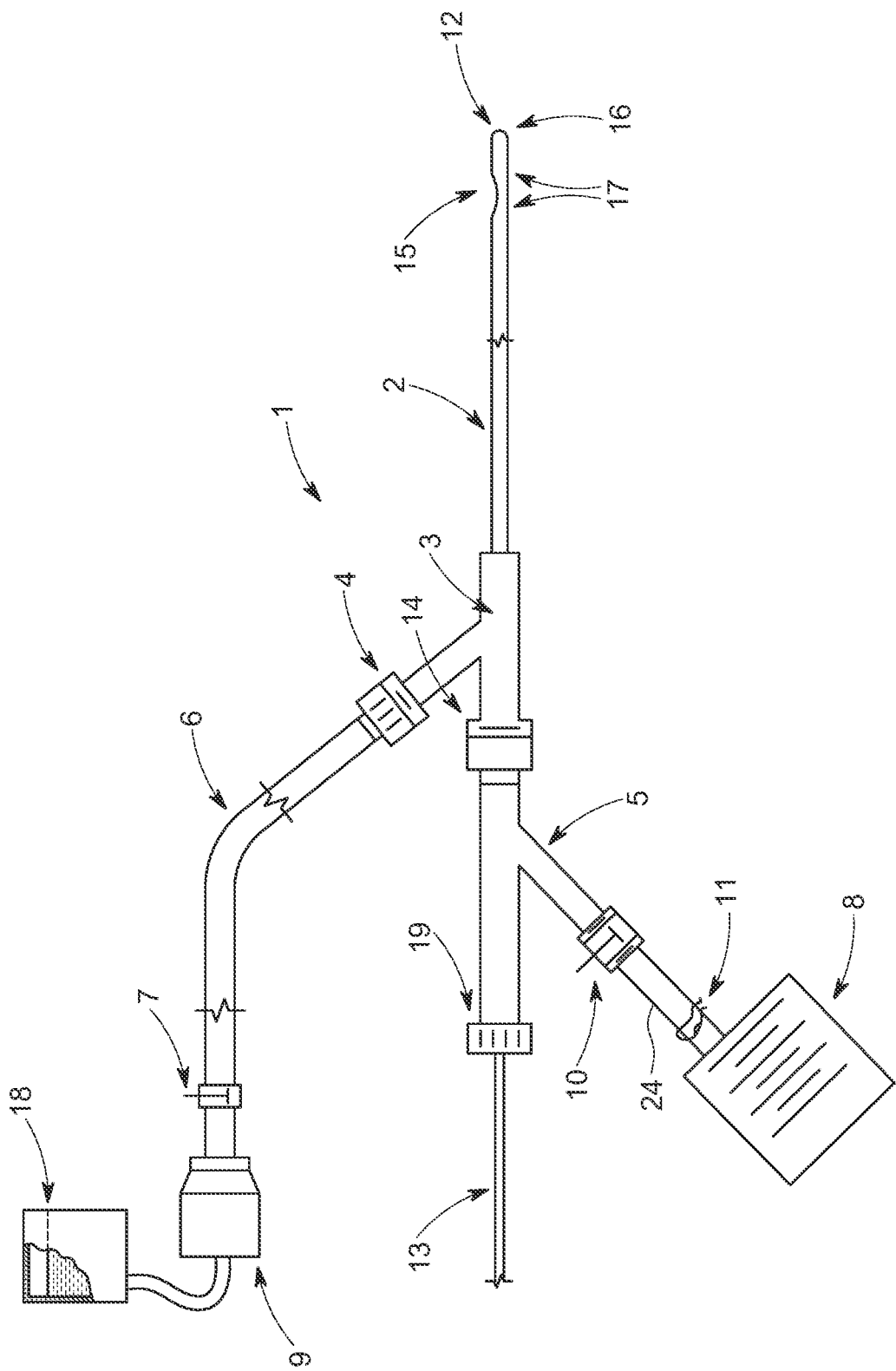
FIG. 1 is an illustration of a suction catheter apparatus of the present invention.

FIG. 1 shows the catheter of the present invention in the use of a suction catheter which comprises a tubular body 2 with a distal end 12 in which a suction opening 15 has been formed. Close to the proximal end the body 2 is connected to a Y-piece 3 which is shown in greater detail in FIG. 2.

Connected with the Y-piece 3 is a first tube 6 to which a pressurized fluid source is connected. In the illustration embodiment, pump 9 draws liquid from a reservoir 18, and delivers the pressurized liquid through pressure channel 25. Furthermore, a discharge tube 24 is connected to the Y-piece 3 leading to a discharge reservoir 8.

The pressure channel 25 may be a lumen defined by the Y-piece 3 and body 2, or by a tube disposed within Y-piece 3 and body 2, connected with a pressure channel in the body 2.

Figure 2:
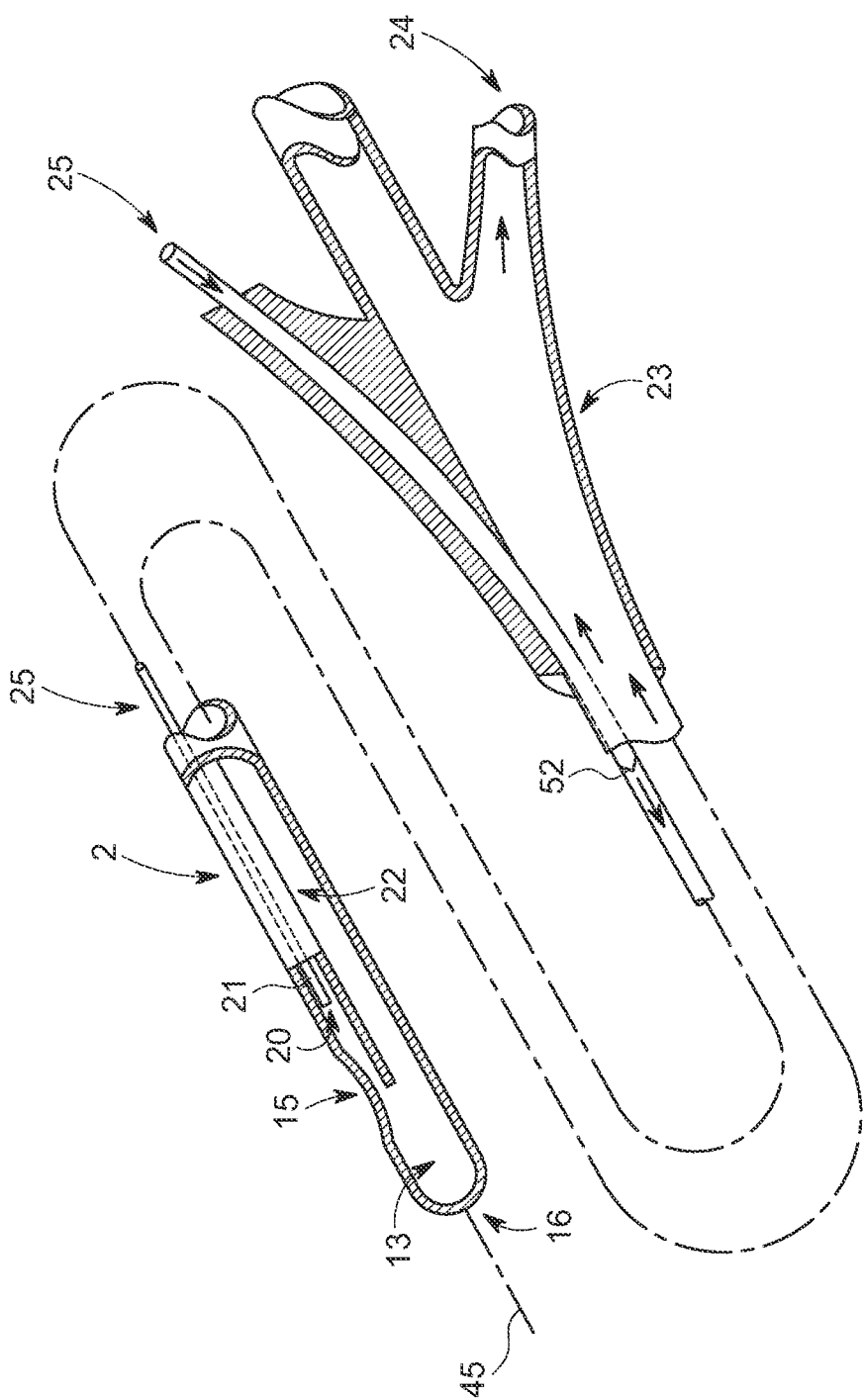
FIG. 2 is an illustration of a portion of the suction catheter apparatus of the present invention.

In FIG. 2, it can be seen that the body 2 of the illustrated catheter 1 comprises a pressure channel 25 and a discharge channel 22.

Figure 3:
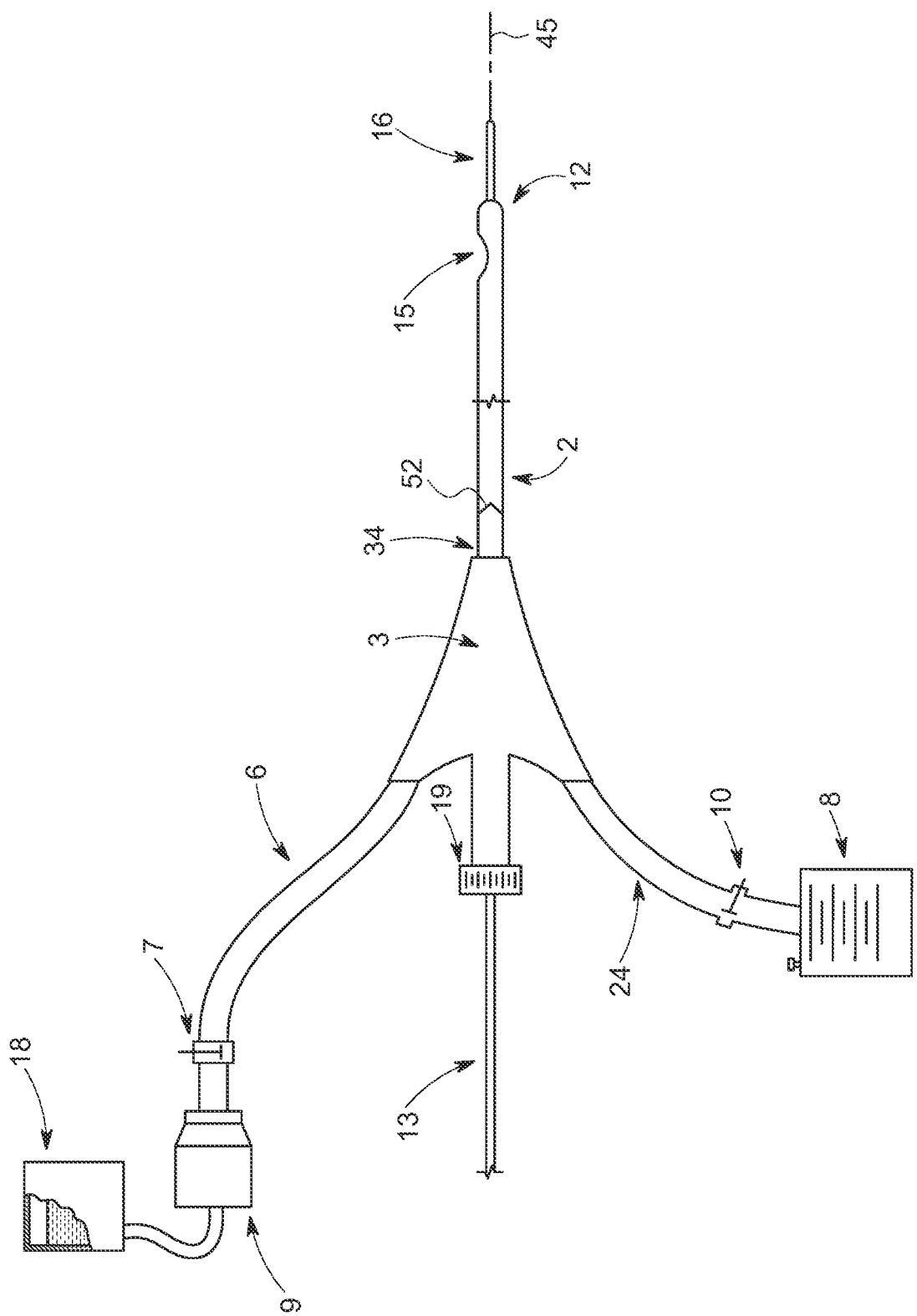
FIG. 3 is an illustration of a suction catheter apparatus of the present invention.

Pressurized fluid is driven by pump 9 through pressure channel 25 in the body 2 toward the distal end 12 of the catheter as shown in FIG. 2 and FIG. 3.

Tube 21 extends from pressure channel 25 to convey and direct pressurized fluid in a specific manner through an emission opening 31 into a chamber 13 that is in fluid communication with the suction opening 15 and discharge channel 22.

Figure 4:
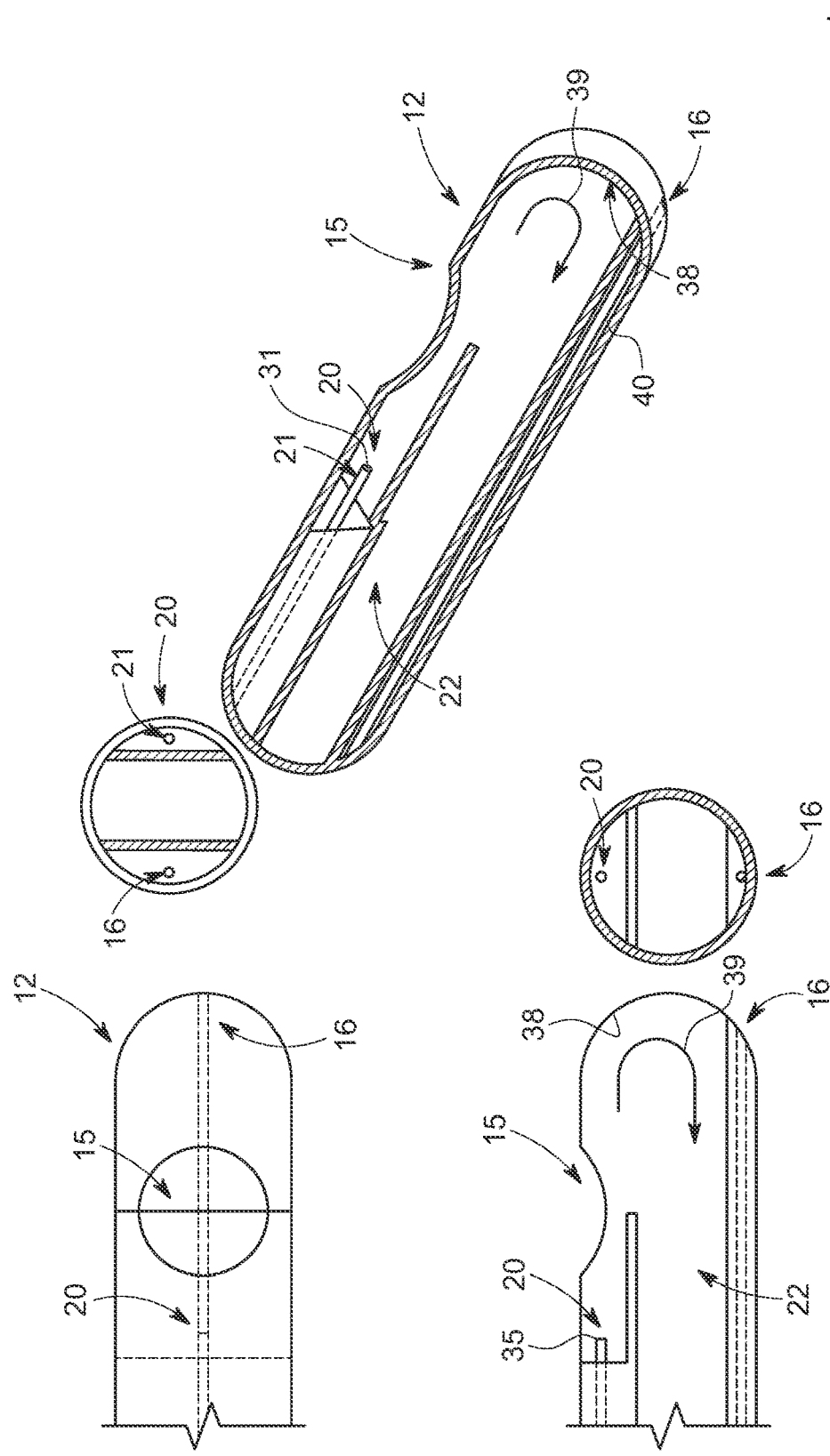
FIG. 4 includes a top plan view, front cross-sectional view, side-cross-sectional view, and perspective cut away view of a distal end portion of a suction catheter apparatus of the present invention.
Figure 5:
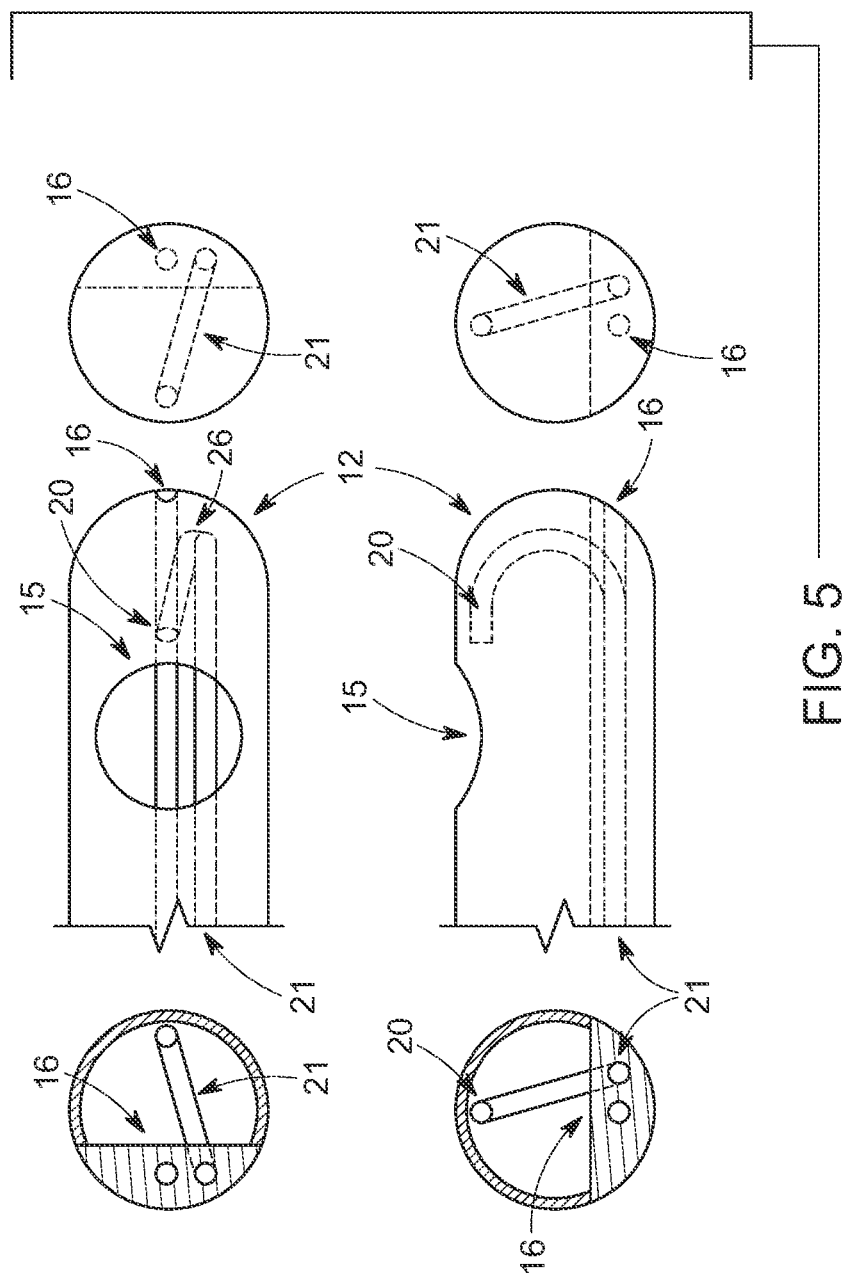
FIG. 5 includes a top plan view and front cross-sectional and front elevational views of such orientation, as well as a side elevational view and front cross-sectional and front elevational views from the side elevational view orientation.
Figure 6:
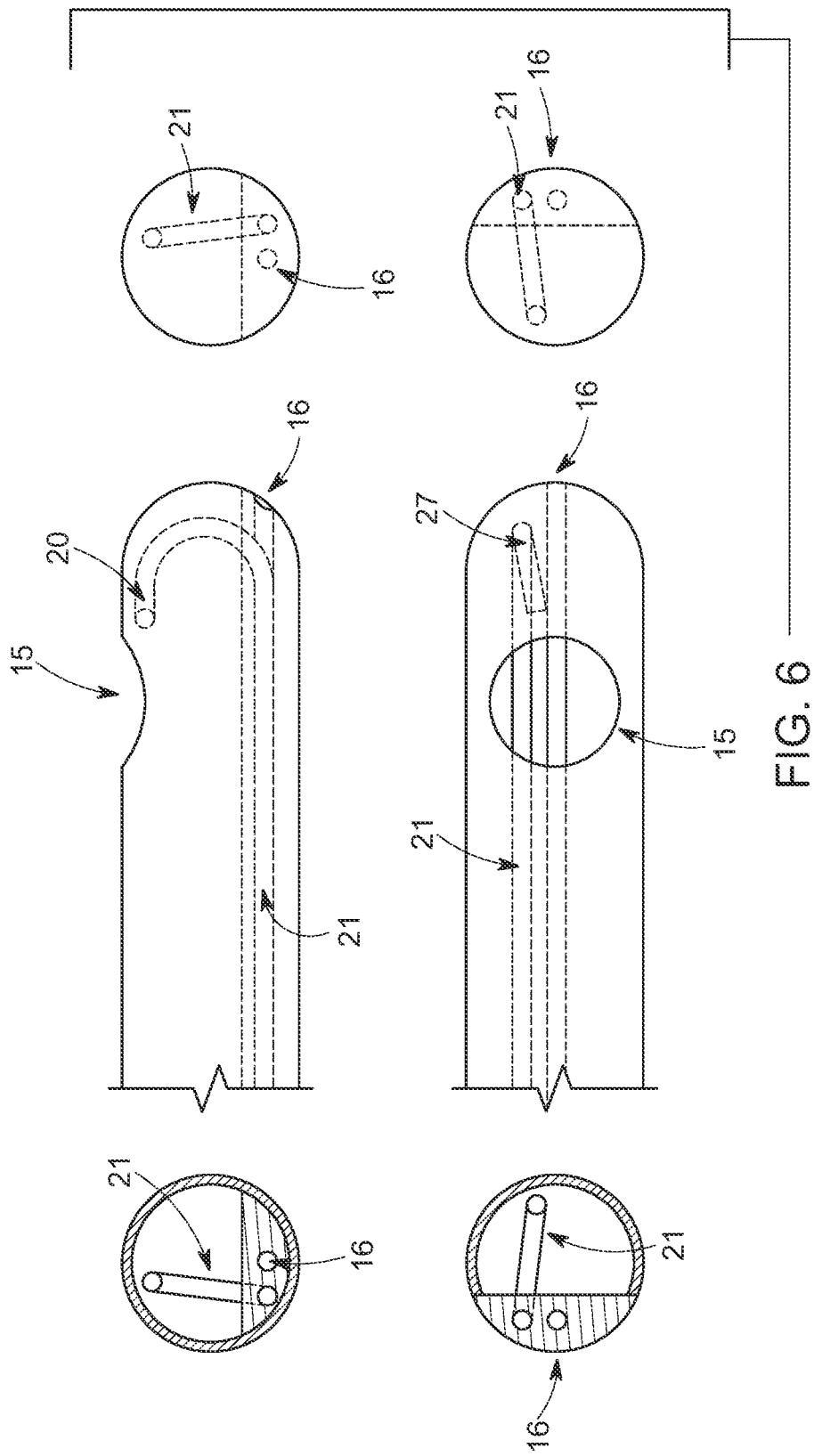
FIG. 6 includes a side elevational view and a rear cross-sectional view and front elevational view of that orientation, as well as a top plan view with a rear cross-sectional view and a front elevational view from the top plan view orientation.

Tube 21 may convey pressurized fluid for emission in a fluid stream 20 in a distal direction past suction opening 15, wherein emission opening 31 is proximal with respect to suction opening 15, as shown in FIGS. 2 and 4. In other embodiments, such as that shown in FIGS. 5-7, tube 20 may convey pressurized fluid for emission in a proximal direction past suction opening 15, wherein emission openings 31 is distal with respect to suction opening 15. Tube 21 (which is illustrated as being straight or U shaped) functions as a jet nozzle and directs the fluid which is delivered through the pressure channel 25 in a carefully controlled manner along the inside of the suction opening 15, so that an ejector action is obtained in a reliable and efficient way. By means of this ejector action, material outside the catheter in the vicinity of the suction opening 15 is sucked through this opening 15 and is carried along in the discharge channel 22 towards the proximal end. As is shown in FIG. 2, a discharge tube 24 connects to the discharge channel 22. Fluid under pressure delivered through the pressure channel 25 is emitted in the form of a jet 20 at a relatively high velocity through the tube 21, thus creating suction at the location of suction opening 15. The removal of material brought into the suction catheter through suction opening 15 via the discharge channel 22 and the discharge tube 24 is supported by means of this suction. Together with the fluid delivered through the pressure channel 25 the sucked up material is removed through the discharge tube 24 to a discharge reservoir such as the discharge reservoir 8 of FIG. 3.

The suction catheter of the present invention includes a tubular body 2 having a proximal end 34 and a distal end 12. The tubular body 2 may include two or more lumens extending from the proximal end 34 to the distal end 12. A first lumen may define a pressurized fluid channel 25 for passage of pressurized fluid from the proximal end 34 to the distal end 12. A second lumen may define a discharge channel 22 for passage of fluid from the distal end 12 to the proximal end 34. Tubular body 2 may include third and fourth lumens as necessary.

A suction opening 15 is formed near the distal end 12 of body 2 to facilitate passage of surrounding fluid and particulate into chamber 13.

A tube 21 having a distal end 35 defining an emission opening 31, extends from pressurized fluid channel 25. Tube 21 may extend from within pressurized fluid channel 25. Tube 21 may, in some embodiments, be shaped in the form of a hook with emission opening 31 directing fluid net 20 proximally. As another possible embodiment, the tube 21 may extend substantially linearly with emission opening 31 directing fluid jet 20 distally. It is contemplated that tube 21 may be variously configured to achieve the ejector action of the present invention. The "ejector action" is a fluidic force applied to material external to the catheter in the vicinity of the suction opening 15.

In all embodiments, the tube 21 includes an emission opening that directs fluid past the suction opening 15.

A discharge channel 22 is configured to convey fluid and material collected through the suction opening 15 proximally toward proximal end 34. Discharge channel 22 may include a directional wall 38 that re-directs fluid flow from a distally-oriented to a proximally-oriented direction, as demonstrated by re-direction arrow 39. In such a manner, fluid flow along discharge channel 22 acts to remove material such as thrombi, emboli, tissue or other particulate from a living body that was drawn into chamber 13 through suction opening 15.

Body 2 may include a third lumen 40 to facilitate passage of existing guidance and support device such as a guidewire 16, to guide the catheter 1 to the desired body location. Body 2 may further include a fourth lumen to, for example, facilitate delivery of physician-specified fluids to the treatment location.

As described above, tube 21 includes an emission opening 31 that orients fluid flow therethrough toward suction opening 15. Emission opening 31 may be at a terminus of tube 21, or may instead be positioned at some point along tube 21. Emission opening 31 fluidically communicates with a lumen defined by tube 21, wherein the lumen of tube 21 is configured to deliver fluid at relatively high velocity and high flow rate. A relatively high exit velocity of the fluid through emission opening 31 is developed through the configuration of the lumen of tube 21, which presents a relatively small cross-sectional area through which the pressurized fluid is forced.

A particular feature of the present invention is the ability of catheter 1 to generate sufficient suction through suction opening 15 to draw target material into chamber 13 while avoiding damage to surrounding tissue, thereby minimizing the risk of distal embolization. In particular, the fluid flow rate and tube 21 lumen diameter are arranged such that the relatively high velocity fluid flow delivered through emission opening 31 ensures that the shear stress applied via suction opening 15 to erythrocytes and other surrounding cells remains at or below a threshold stress level of 20,000 N/m$^2$ that is estimated to cause cell damage. As an example, a potential flow rate of 3 mL/s through a 0.05 cm diameter emission opening 31 may result in a maximum shear stress applied to the erythrocytes in the vicinity of suction opening 15 of well below 20,000 N/m$^2$. The fluid flow exiting through emission opening 31 of tube 21 creates a pressure differential between the suction opening 15 and the surrounding fluid, resulting in the movement of material from the area surrounding body 2 into suction opening 15. This pressure differential across two separate fluid domains is not based on the Bernoulli principle.

Subsequent to passing by suction opening 15, the fluid jet 20 may impinge upon discharge channel 22, thereby establishing an elevated pressure area inside discharge channel 22 to facilitate the removal of collected material along discharge channel 22 in a proximal direction toward proximal end 34, and eventually out from the patient. A collection chamber 8 may be coupled to discharge tube 24, which itself is fluidically connected to discharge channel 22 for collecting the removed material.

The distal end 12 of body 2 may be formed into a 3-dimensional bend to define a fluid flow redirection means. The bend may feature one or more of an axial and a radial component. The bend forces the fluid jet 20 exiting from emission opening 31 of tube 21 and crossing the suction opening 15 to flow in a skew path which is not parallel to a longitudinal axis 45 of the body 2. An example fluid flow re-direction means includes re-direction wall 38.

The distal end 35 of tube 21 may be separately formed into a 3-dimensional bend forming another fluid flow re-direction means. The bend of tube 21 may feature an axial and a radial component. The bend forces the fluid exiting from emission opening 31 at the distal end 35 of tube 21 and crossing the suction opening 15 to flow in a skew path which is not parallel to longitudinal axis 45. The radial and axial angles of the skew path may range from between 5° to 45° with respect to longitudinal axis 45.

The two separate bends described above force the fluid jet 20 crossing the suction opening 15 to follow a path which may be skewed both with respect to the axis of the proximal end 34 of the body 2 and with respect to the longitudinal axis 45, thus inducing a rotational momentum into the surrounding fluid. The resulting vortex in the fluid surrounding body 2 destabilizes the material to be removed, further assisting in its removal.

In some embodiments, a valve 52 may be incorporated near proximal end 34 of body 2 to allow high-frequency cycling or pulsation of the pressurized fluid in pressure channel 25. Valve 52 may comprise a high-frequency movable member that generates high-frequency longitudinal waves which are propagated through the pressurized fluid inside pressure channel 25 and at distal end 12 to further destabilize the material surrounding body 2 targeted to be removed. Valve 52 may be operated with an open/close cycle of between 0.5-10 Hz.

The distal end 12 of the body 2 may incorporate an outflow side orifice allowing pressurized fluid to flow into the surrounding area at high velocity to further destabilize and detach the material to be removed. The said outflow side orifice may be alternatively incorporated into the fourth lumen.

As appears clearly from the figures, the catheter according to the invention with the combined pressure connection for the pressure channel and pressure inlet for the liquid jet pump, is just as easy to use as the previously known hydrodynamic suction catheter. Compared with the known catheter there are no additional connections while the catheter according to the invention can be manufactured with a greater length and a smaller diameter.

The invention has been described herein in considerable detail in order to comply with the patent statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. A suction catheter apparatus, comprising:

a tubular body having a proximal end portion and a distal end portion, and a suction opening at the distal end portion for collecting material from a region external to the distal portion, the tubular body defining at least first and second lumens extending from the proximal end portion to the distal end portion, each of the first and second distinct lumens in fluid communication with a chamber defined within the distal end portion of the tubular body, the chamber being in fluid communication with the suction opening, the distal end portion of the tubular body defining a longitudinal axis coincident with or parallel to a central axis circumaxially around which is formed a side wall of the tubular body;

a tube extending from the first lumen of the tubular body into the chamber and defining a tube channel and an emission opening in fluid communication with the tube channel, the emission opening being positioned and oriented in combination with the tube channel to direct fluid flow from the tube channel into an emission jet that emits in a proximal to distal direction from the emission opening into the chamber and is flowable within the chamber and past the suction opening in a manner to create an ejector action upon the material;

a connector secured to the proximal end portion of the tubular body and having an inlet coupling portion and an outlet coupling portion, the inlet coupling portion having an inlet lumen in fluid communication with the first lumen of the tubular body, and the outlet coupling portion having a separate outlet lumen in fluid communication with the second lumen of the tubular body;

a pump for delivering pressurized fluid from a fluid reservoir to the chamber through the inlet lumen, the first lumen, and the tube channel; and a collection chamber in fluid communication with the outlet lumen for collecting the material through the second lumen.

2. The suction catheter as in claim 1 wherein the tube is substantially linear throughout its length.

3. The suction catheter apparatus as in claim 1, including a third lumen in the tubular body.

4. The suction catheter apparatus as in claim 3, including a guide wire extendable through the third lumen.

5. The suction catheter apparatus as in claim 1, including a fourth lumen in the tubular body.

6. The suction catheter apparatus as in claim 1, including a directional wall defining a portion of the chamber and being configured to re-direct the distally-directed emission jet to a proximally-directed fluid flow.

7. The suction catheter apparatus as in claim 6 wherein the proximally-directed fluid flow is directed through the second lumen.

\* \* \* \* \*